United States Patent [19]

Byers et al.

[11] Patent Number: 4,553,034
[45] Date of Patent: Nov. 12, 1985

[54] ION EXCHANGE RESIN INTRUSION MONITOR

[75] Inventors: William A. Byers, Penn Hills; Steven H. Peterson, Murrysville, both of Pa.

[73] Assignee: Westinghouse Electric Corp., Pittsburgh, Pa.

[21] Appl. No.: 557,569

[22] Filed: Dec. 2, 1983

[51] Int. Cl.$^4$ .......................... G01N 21/38; G01J 1/58
[52] U.S. Cl. .................................................. 250/458.1
[58] Field of Search .................... 73/36, 37.6, 40, 40.5, 73/53, 61 R; 250/227, 337, 458.1, 459.1, 461.1, 574, 373, 484.1; 356/317, 318, 417

[56] References Cited

U.S. PATENT DOCUMENTS

| | | | |
|---|---|---|---|
| 3,163,767 | 12/1964 | Witt et al. | 250/227 |
| 3,289,003 | 11/1966 | Jorgenson | 250/565 |
| 3,462,608 | 8/1969 | Weston et al. | 250/576 |
| 3,636,917 | 1/1972 | Baker | 118/9 |
| 3,917,945 | 11/1975 | Sema et al. | 250/461.1 |
| 3,924,951 | 12/1975 | Dittrich | 356/102 |
| 3,940,608 | 2/1976 | Kissinger et al. | 250/227 |
| 4,127,773 | 11/1978 | West | 250/461.1 |
| 4,284,355 | 8/1981 | Hansen et al. | 356/335 |

FOREIGN PATENT DOCUMENTS 1232581  5/1971  United Kingdom ................ 250/484

OTHER PUBLICATIONS

S. J. Elmiger, J. M. Kibler, E. D. Yochheim & W. D. Mills, "Procedure for the Measurement of Resin Fragment Leakage: Preliminary Results From the Davis Besse Nuclear Station", Proceedings of the 41st International Water Conference, Pittsburgh, PA, 1980, p. 250.

R. J. Gartmann, "Techniques for the Measurement and Reduction of Resin Carry-Over from Condensate Polishers", Proceedings of the 42nd International Water Conference, Pittsburgh, PA, 1981, p. 289.

Primary Examiner—Alfred E. Smith
Assistant Examiner—Vincent J. Lemmo
Attorney, Agent, or Firm—L. A. DePaul

[57] ABSTRACT

Process and monitor for detecting the presence of particles in an effluent fluid, which particles emit fluorescent light upon irradiation. As used to monitor ion exchange resin fines in effluent liquid in a steam power plant, there are probe means to inject fluorescence-stimulating light into a volume of the effluent liquid. Detector means are disposed to receive emitted fluorescent light from any particles in the effluent, and there are means actuatable by said detector means for generating a signal to indicate the presence of particles in the effluent.

15 Claims, 4 Drawing Figures

ION EXCHANGE RESIN INTRUSION MONITOR

BACKGROUND OF THE INVENTION

1. Field of the Invention

This invention relates to an on-line, fiber optics monitor for the detection of resin fluorescence of ion exchange resin particles entrained in water. The monitor is especially useful for sensing resin leakage from condensate polishers and make-up demineralizers in steam power plants.

2. Background

Electric utilities require water of extremely high purity for the production of steam. This purity is usually achieved by the use of ion exchange systems commonly referred to as demineralizers, polishers, or deionizers.

Harmful cationic and anionic materials are removed from solution by passing the raw water through vessels containing ion exchange resins. In deep bed systems, the resin takes the form of small spherical beads ($\sim 1$ mm. dia.). The beads are usually contained in beds in large tanks which are screened at the top and bottom. Alternatively, the resin may take the form of a powder that is coated onto tubular filters.

A common problem with such demineralizer systems is resin leakage. This occurs when resin particles are broken into small fragments by mechanical, physical or chemical action, and the fragments then pass through screens and filters designed to retain the resin. Leakage may also result from defective filters and screens or improper operation. The fines can be carried into high temperature regions of a plant where they decompose to form corrosive compounds. Both cation and anion exchange resins decompose at temperatures above 200° C. to yield ionic products which can be very corrosive in both gaseous and liquid phases.

Despite the importance of detecting resin intrusions, little is available in the way of instrumentation for this purpose. The only approach which appears to have been used to date is filter collection. This approach is described in *Procedure for the Measurement of Resin Fragment Leakage: Preliminary Results from the Davis Besse Nuclear Station*, by S. J. Elmiger et al., Proceedings of the 41st International Water Conference, Pittsburgh, Pa, 1980, pages 250-254. This technique utilizes a collecton procedure that involves insertion of a sampling tube into the demineralizer effluent with filtering of the flow from this tube with a microporous filter having, for example, a 0.45 micron pore size. The filter is then dissolved and the volume of resin is measured in a centrifuge tube. Alternatively, the fines are counted while on the filter by microscopic examination. This type of method gives batch-wise information. The sampling can be non-representative, the technique is laborious, and non-resin particulate matter can interfere.

SUMMARY OF THE INVENTION

The present invention is a monitor that can provide a continuous measure of ion exchange resin particle concentration in water, can measure resin particle size, and can determine the identities of the resin particles, that is, whether anionic or cationic. The monitor may also be used to control the operation of a demineralizer in a power plant.

In one broad embodiment, the invention is a monitor for detecting the presence of ion exchange resin particles in a water flow channel that receives effluent from an ion exchange system, such as the ion exchange system in a steam power plant. This monitor is a combination of several elements. A first element is a probe means comprising a first bundle of optical fibers disposed to inject fluorescence-stimulating light into a volume in the water flow channel. The monitor also comprises detector means, preferably comprising a second bundle of optical fibers. The detector means is disposed to receive fluorescent light emitted from any particles in the effluent passing through the illuminated volume in the flow channel. In addition, the monitor comprises means for receiving emitted fluorescent light from said second bundle of fibers, actuatable thereby for generating a signal to indicate the presence of particles in the effluent.

In another embodiment, the invention is a process for detecting the presence of fluorescent particles in a flow of fluid. This process comprises injecting fluorescence-stimulating light into a volume of the fluid, and then detecting any fluorescent light emitted by any particles in the volume of fluid that was irradiated.

DETAILED DESCRIPTION OF THE PREFERRED EMBODIMENT

This invention is based on the important feature of UV-visible light spectroscopy that lends itself to quantitative analysis. Fluorescent light is light that is emitted from a certain type of molecule, after the molecule has been illuminated by light of higher energy (shorter wavelength). In a typical manifestation of the fluorescent phenomenon, a fluorescent molecule is illuminated with high energy-short wavelength light and it absorbs this energy, then re-emits it as fluorescent light of lower energy and longer wavelength.

Both cation and anion exchange resins exhibit fluorescent properties. When particles of these resins are illuminated or irradiated with fluorescence-stimulating, short wavelength light, the resin molecules absorb the light and emit fluorescent light.

The phenomenon of fluorescence is utilized in the present invention for the selective detection of the presence of ion exchange resin particles in the aqueous effluent from an ion exchange system. While such an effluent may contain many different types of particles, generally only the resin fragments exhibit fluorescence, so that the monitor of the invention detects their presence selectively.

Since fluorescence measurements can be extremely sensitive, the detection monitor of this invention can detect very low levels of resin particles with great sensitivity.

Figure 1:
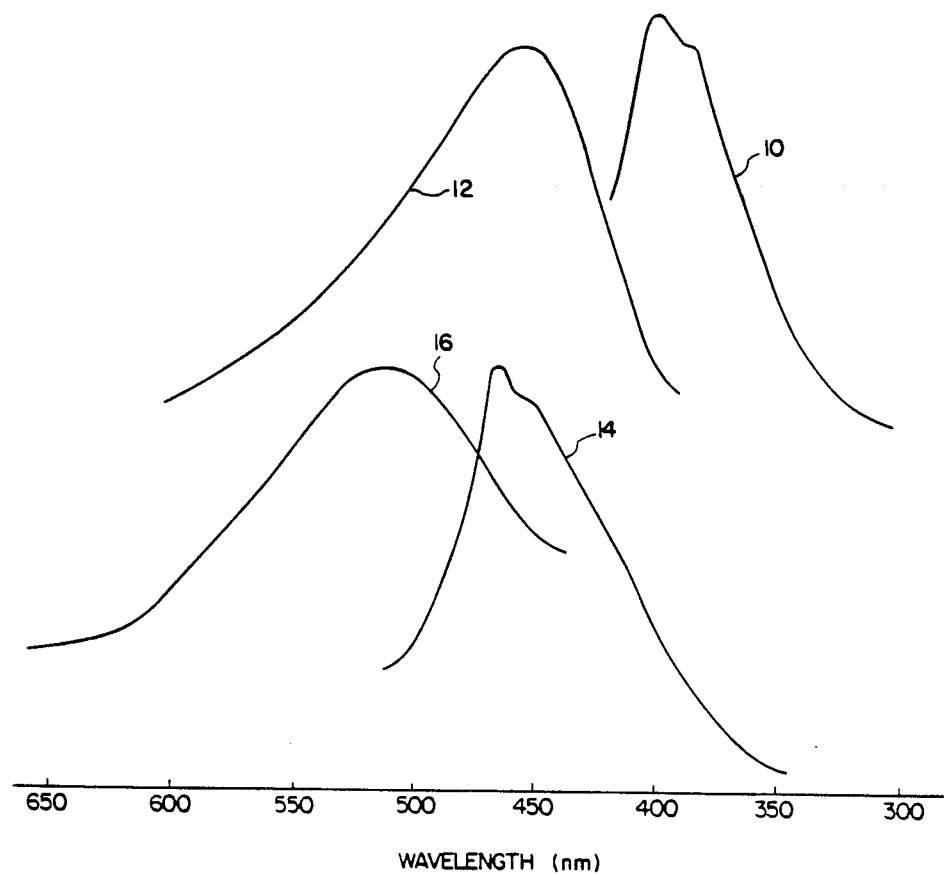
FIG. 1 is a graphic representation showing how specific resin particles respond to exciting (fluorescence-stimulating) light over a band of wavelengths by emitting (fluorescing) light in a different band of longer wavelengths.

Referring now to FIG. 1, the numeral 10 denotes graphically the wavelengths of light energy that will excite an anion exchange resin in the chloride form, and thus stimulate fluorescent emission. The wavelengths of the emitted fluorescent light are shown by the curve 12 in FIG. 1.

Similarly, the numeral 14 denotes graphically the wavelengths of light that will stimulate emission by a cation exchange resin in the hydrogen form. The curve of emitted fluorescent light is depicted by the line 16.

The spectra for these two resins were obtained with an FOCI Mark I Spectrofluorimeter. To obtain the data for plotting these curves, the cell was partially filled with a mixture of resin and water. The cell was then illuminated with a wavelength that the resin would absorb.

The anion exchange resin fluoresces in the blue region, whereas the cation exchange resin fluoresces primarily in the green region. This permits these two different types of resin to be identified. However, there is enough overlap in the spectra so that both resin types may be detected simultaneously at a single wavelength.

Figure 2:
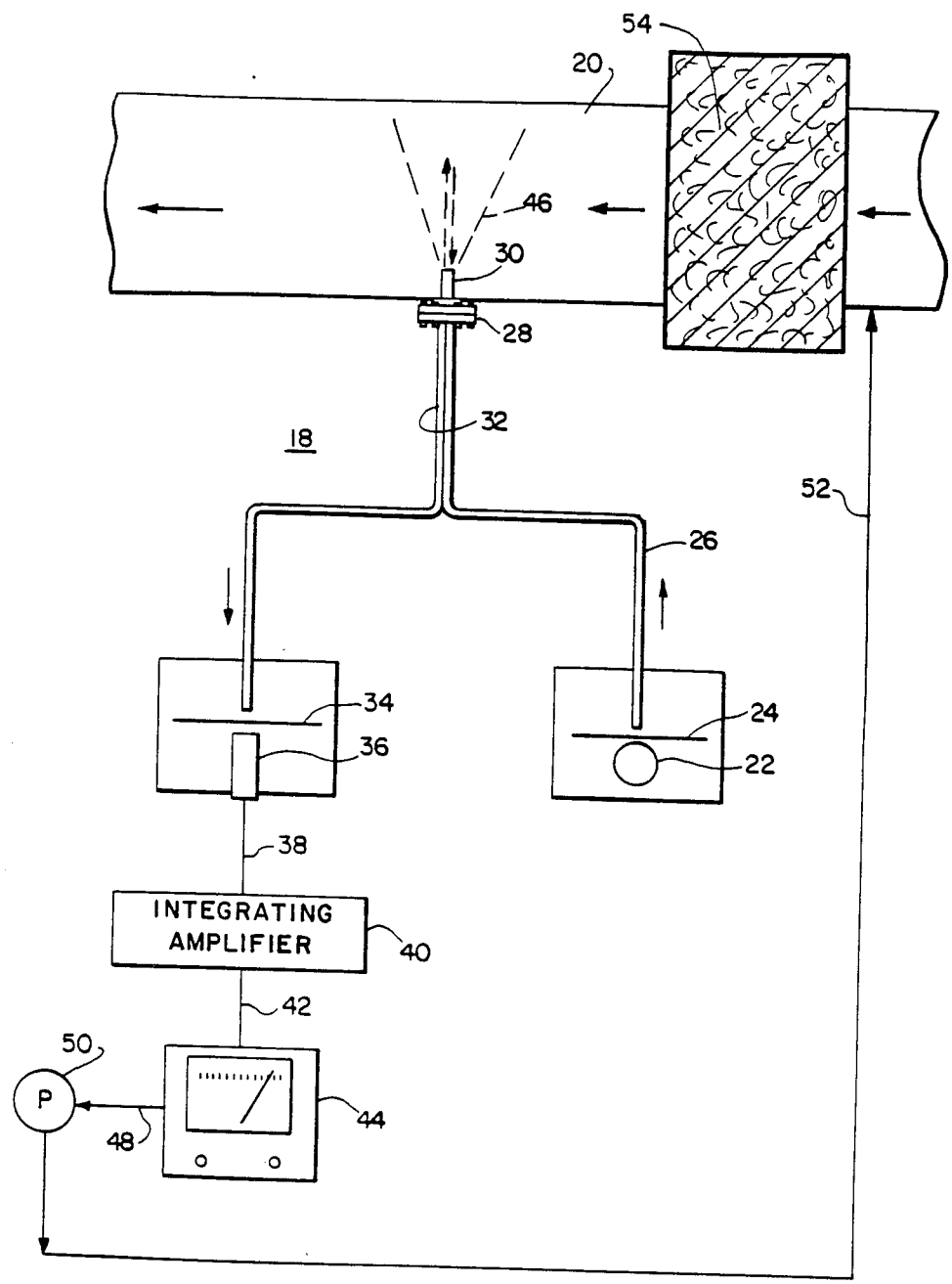
FIG. 2 is a fragmentary schematic diagram showing a monitor constructed in accordance with one embodiment of the invention and arranged to detect resin particle leakage from a mixed bed ion exchange system and to control the amount of recirculation of effluent from the system through a filter.

Referring now in detail to FIG. 2, in one preferred embodiment, the monitor 18 is mounted to detect the presence of resin particles in an effluent flowing through a pipe 20, the direction of flow being indicated by an arrow. The monitor comprises a probe assembly for injecting fluorescence-stimulating light into the effluent, means for detecting emitted fluorescent light, and generating means, actuatable by the detector means in response to emitted fluorescent light, for generating the signal to indicate the detection of particles in the effluent.

The probe assembly consists of a xenon arc lamp 22. A 400 nm interference filter 24, having a 10 nm FWHM bandpass, is disposed adjacent the xenon arc lamp 22. A bundle of optical fibers 26 is disposed to receive light emitted from the xenon arc 22 and passing through the interference filter 24. This fiber bundle 26 is encased in a length of protective tubing which is not shown in the drawing for simplicity of illustration. The tubing, containing the fiber bundle 26, is extended to a flanged fitting 28 that secures the tubing and the bundle 26 to the pipe 20, in water-tight fashion.

A short length of tubing 30 projects from the flanged fitting 28 a short distance into the interior of the pipe 20. The end of the tubing 30 that is within the pipe is terminated with a silica window (not shown). The fiber optic bundle 26 extends in one continuous length from its lower end (relative to FIG. 2) adjacent the interference filter 24, to an upper end terminating at the silica window inside the pipe 20.

The means for detecting emitted fluorescent light comprises a second bundle of optical fibers 32, whose upper end also terminates at the silica window at the upper end of the short length of tubing 30. For protection of the fiber bundle, it may also be enclosed within a protective tubing (not shown).

To permit the detection of cation and anion exchange resin particles with approximately equal sensitivity, a 490 nm interference filter 34 with a 10 nm bandpass is disposed at the lower end of the fiber optics bundle 32, to intercept fluorescent light transmitted by the fiber bundle. A photodiode 36 is disposed adjacent the filter 34 to receive light passing through the filter 34. The photodiode 36 is connected through a line 38 to an integrating amplifier 40. The output from the amplifier 40 is transmitted through a line 42 to a recorder 44 or other device.

The two interference filters 24 and 34 respectively are mounted to be easily replaced by other optical filters, so that the monitor can be used to inject other fluorescence-stimulating light and to be responsive to other wavelengths of emitted fluorescent light.

In use, to detect fines flowing through the pipe 20 in effluent from a mixed ion exchange resin bed in a demineralizer of a steam power plant, the arc lamp 22 is energized. The light from this broad band source passes through the filter 24 and along the fiber optics bundle. This light is directed from the upper end of the fiber optics bundle into the effluent, where it illuminates a generally cone-shaped volume 46 of the effluent stream.

The cone-shaped volume 46 of effluent that is illuminated should be sufficiently large so that multiple resin fines, if present, are illuminated or irradiated at any one time. Those fines within the cone-shaped volume 46 that are irradiated emit fluorescent light. Some of the emitted fluorescent light impinges on the upper end of the short length of tubing 30 that contains the second bundle 32 of optical fibers. This light is transmitted by the fiber bundle 32 through the interference filter 34 to activate the photodiode 36. The integrating amplifier 40 receives the output from the photodiode 36 and smooths the signal. Particularly at low leakage rates of fines, this signal may be irregular. The signal from the integrating amplifier 40 should be proportional to the intensity of fluorescent light transmitted to the photodiode 36 and thus proportional to the concentration of resin fines in the effluent flowing through the pipe 20.

The signal generated by the integrating amplifier 40 can be transmitted to a meter 44 on a recording device, for display. For greatest usefulness, the meter should be equipped with zero and slope adjustments for calibration. If desired, the output signal thus generated can be transmitted not only to a recorder-meter as shown, but also to a data acquisition system or demineralizer controller.

Thus, as shown very schematically in FIG. 2, the signal can be transmitted from the recorder-meter 44 through a line 48 to control a system connected to the effluent line 20 that includes a pump 50. This pump 50 may be connected to recirculate the effluent from the line 20 through appropriate piping 52 to a location upstream of a filter 54 through which the effluent must pass to enter the line 20. Thus the signal generated by the monitor could be used to induce recirculation of demineralizer effluent after a regeneration of a filter coating on the filter 54, until, for example, the leakage rate dropped below a predetermined level. The signal generated could also be used to optimize the rate of flow through the demineralizer so as to minimize the rate of resin leakage.

The monitor has considerable versatility. Thus the interference filter 34 can be replaced with other filters that are of slightly higher or lower wavelengths, to permit a determination of the identity of the resin fines as either cation fines or anion fines, or a mixture. Leakage of cation exchange resins will be indicated if using a longer wavelength filter increases the signal, for example.

Figure 3:
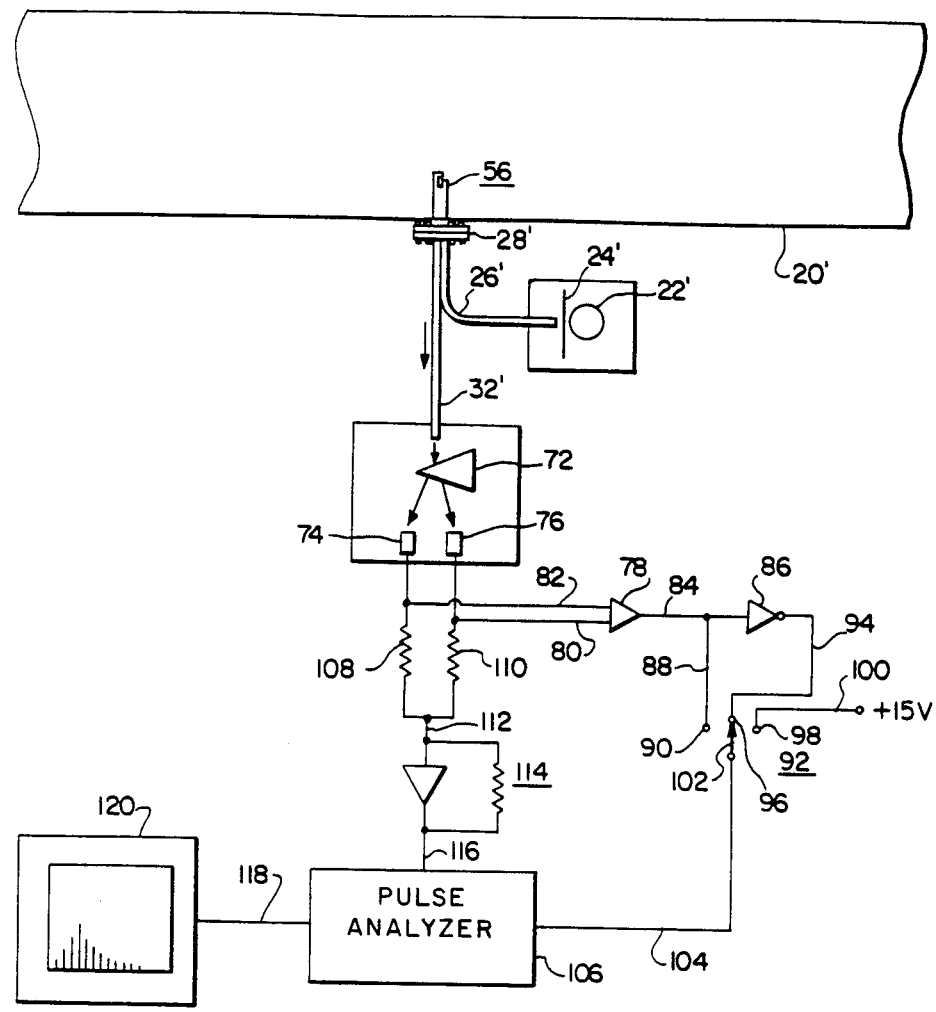
FIG. 3 is a fragmentary schematic diagram of a monitor constructed in accordance with another embodiment of the invention and having great sensitivity, for the purpose of detecting individual particle fragments in the effluent, then generating a signal that is proportional to the size of the particle, to permit not only counting of the individual particles but also an appraisal of particle size.
Figure 4:
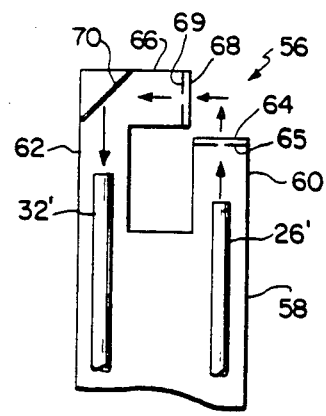
FIG. 4 is a fragmentary section, on an enlarged scale, of a portion of FIG. 3.

Referring now to the modified embodiment of the invention illustrated in FIGS. 3 and 4, we find that there are many elements in the modified embodiment of the invention that are identical with those in the embodiment illustrated in FIG. 2. Thus, the xenon arc lamp 22' is disposed adjacent an interference filter 24', through which filtered radiation enters a bundle 26' of optical fibers. The fiber bundle is connected through a flanged fitting 28' to have a probe head 56 projecting into the effluent stream flowing through the pipe 20'. The probe head 56, shown on an enlarged scale in FIG. 4, is constructed and arranged in such a way that the probe views only a very small volume of the effluent stream, so that single resin particles can be counted. Thus, the probe head 56 is formed with a housing 58. This housing is bifurcated at its upper end, so that there is an opening between a light input arm 60 and a light output arm 62.

The light input arm 60 is closed at its upper end by a window 64. The end of the bundle of fibers 26' carrying fluorescence-stimulating light is disposed a short distance below the window 64.

The light output arm 62 is formed with a generally horizontally extending arm 66. The end of this arm is closed with a window 68 that is transparent to fluorescent light. The window 68 is part of an optical system that includes a mirror 70 that is mounted to receive light from the window 68 and direct it to the upper end of the second bundle 32' of optical fibers.

A disperser prism 72 is mounted below the lower end of the second fiber bundle 32', and is positioned so as to divide any transmitted light that impinges on the disperser, as shown by the arrows in the drawing.

A pair of photodiodes 74, 76 respectively are disposed beneath the disperser 72, in positions to receive different wavelengths of light respectively from the disperser 72.

The supporting electronics for the photodiodes include a comparator 78 that is electrically connected to the two photodiodes respectively by a pair of lead lines 80 and 82. The comparator 78 is also connected through a line 84 with an inverter 86. The line 84 is connected through a line 88 to one terminal 90 of a selector switch that is generally designated by the numeral 92. The second terminal of the inverter 86 is connected through a line 94 to a second terminal of the selector switch 92. The third terminal 98 of the selector switch is connected through a line 100 to a source of DC Voltage at +15 volts. The armature 102 of the selector switch is connected through a line 104 to one terminal of a multi-channel pulse height analyzer 106.

A pair of resistors 108, 110 are connected respectively to the lead lines 82, 80 that in turn connect with the two photodiodes. The lower terminals from these resistors 108, 110 are interconnected and communicate through a line 112 with one terminal of an addition amplifier 114. The other terminal of the addition amplifier is connected through a line 116 with a second terminal of the multi-channel pulse height analyzer 106. A third terminal of this analyzer is connected through a line 118 with a cathode ray tube display device 120. The electronics can be designed so that the screen of the CRT display device shows a display similar to a bar chart, indicating the relative numbers of particles of given different sizes that are detected by the device.

In this monitor, the probe head views only a very small volume of the passing effluent liquid. This permits single resin particles to be counted. Each resin particle will produce a peak which is proportional to its size. The distribution of such fines over a given time period can then be recorded and displayed using a multi-channel peak height analyzer 106, as shown in the drawing. The instrument can be set, by adjustment of the armature 102 of the selector switch 92, to record detected cation fines, anion fines, or total fines. For this purpose, the armature 102 can be moved to one of the three terminals 90, 96 or 98, respectively, to apply to the line 104 and thus to one terminal of the multi-channel pulse height analyzer 106 a voltage of +15 volts or −15 volts. A voltage of +15 V enables particle counting, while a voltage or −15 V disables particle counting.

In the embodiment of the invention illustrated in FIGS. 3 and 4, the elements in the probe head that inject fluorescence-stimulating light into the effluent stream preferably do so through a slit in a screen 65 that is interposed between the end of the fiber bundle 26' and the window 64. The light emerging from the slit does so as a ribbon of light rays arranged in a generally planar manner, with the plane being parallel to the direction of flow of the liquid effluent. Similarly, any emitted fluorescent light that passes through the window 68 also passes through a slit in a screen 69 that is disposed intermediate the window 68 and the mirror 70. The effect is to restrict the detection capabilities of the monitor to an extremely limited volume. While a preferred arrangement is the one shown in FIG. 4, where the input radiation and the emitted fluorescent rays that are monitored are generally at right angles to each other, they could be essentially parallel to each other as in the monitor shown in FIG. 2, or alternatively, at some angle to each other other than the right angle shown in FIG. 4.

CONCLUSION

Monitors constructed in accordance with the invention can be used for a variety of purposes in addition to those discussed here. Another application for the probe illustrated in FIG. 2, for example, is mixed bed resin monitoring. A probe placed within the resin bed can be used to determine the degree of cation-anion resin separation.

The invention has been described above in connection with the use of fluorescence spectroscopy and fiber optics to provide a continuous measure of ion exchange resin particle concentration in water, to measure resin particle size, and to determine the identity of resin particles. However, monitors using the technology of the invention can also be used to determine the presence of particles, that can be stimulated to emit fluorescent light, in any type of fluid stream, whether gaseous or liquid. Such monitoring as is provided by equipment constructed in accordance with the present invention can be extremely valuable in connection with monitoring steam in nuclear plants, for example.

The use of fiber optics in monitors according to the invention is very advantageous in steam power plants. Installations in such plants are subject to extremes of vibration. Such vibration might well render conventional optical systems inoperative. With fiber optics, however, many of the problems associated with intense vibration activity can be avoided or eliminated because of the flexible nature of the optical fiber bundles. It is preferred that the bundles be protected by appropriate sheathing, for their own protection. Such sheathing preferably is formed from plastic material but may be metallic.

Although the present invention has been described with reference to preferred embodiments, it should be understood that the invention is not limited to the details thereof. A number of possible substitutions and modifications have been suggested in the foregoing detailed description, and others will occur to those of ordinary skill in the art. All such substitutions and modifications are intended to fall within the scope of the invention as defined in the appended claims.

What is claimed is:

1. A monitor for detecting the presence of fluorescent particles of ion exchange resin in a water flow channel that receives effluent from an ion exchange system comprising
   (a) probe means comprising a first bundle of optical fibers disposed to inject fluorescence-stimulating light into said water flow,
   (b) detector means disposed to receive emitted fluorescent light from any particles in said water illuminated by the light emitted from said probe means,
   (c) means actuatable by said detector means for generating a signal to indicate the presence of particles in said water; and
   (d) adjustment means to adjust the water flow rate in said ion exchange system to a value which minimizes resin leakage.

2. A monitor in accordance with claim 1 comprising means for injecting into said first bundle of optical fibers fluorescence-stimulating light of a band of wavelengths selected to stimulate any fluorescent resin particles on which it impinges to emit fluorescent light.

3. A monitor in accordance with claim 2 in which said light injecting means comprises a broad-band light source and an interference filter that is disposed intermediate said source and said first bundle to filter the light passing into said first bundle.

4. The monitor of claim 1 wherein said means for generating a signal comprises means for generating a signal that is proportional to the intensity of the fluorescent light emitted by any particles in said water.

5. The monitor of claim 1 wherein said detector means comprises a second bundle of optical fibers, disposed to transmit emitted fluorescent light to said signal generating means.

6. The monitor of claim 5 wherein said means actuatable by said detector means comprises an interference filter that is disposed intermediate said second bundle and a sensing means that is responsive to the light band passed by said filter.

7. The monitor of claim 6 wherein said interference filter is selected to pass a band of wavelengths of emitted fluorescent light that corresponds generally to the peak areas of emission curves that are characteristic of particles of the resin that is in use.

8. A monitor in accordance with claim 1 for detecting the presence of fluorescent particles of ion exchange resin in a water flow channel that receives effluent from an ion exchange system, wherein said probe is disposed in a flow channel downstream of a filter, and where the signal generated by said monitor is used to induce recirculation of effluent flow containing particles back through said filter when the signal is greater than a set level.

9. A monitor for detecting the presence of ion exchange resin particles in a water flow channel that receives effluent from an ion exchange system, comprising
   (a) a xenon arc lamp for emitting fluorescence-stimulating light,
   (b) a 400 nm interference first filter having a 10 nm FWHM bandpass disposed near said lamp for filtering the light emitted from said lamp while passing fluorescence-stimulating light of a band of wavelengths selected to stimulate resin particles on which it impinges to emit fluorescent light,
   (c) a first bundle of optical fibers arranged to receive the light passed through said first filter and to inject the light into a volume of effluent passing through said channel,
   (d) a second bundle of optical fibers disposed to receive emitted fluorescent light from any particles in said effluent passing through said volume of said flow channel,
   (e) a 490 nm interference second filter having a 10 nm bandpass disposed near said second bundle for filtering the light emitted from said second bundle while passing a band of wavelengths of emitted fluorescent light that corresponds generally to peak areas of emission curves that are characteristic of particles of the resin that is in use, and
   (f) signal generating means actuatable by the light emitted from said second bundle for generating a signal that is proportional to the intensity of the fluorescent light emitted by the particles in said effluent and to indicate the presence of particles in said effluent,
   said second bundle of optical fibers being disposed to transmit fluorescent light to said signal generating means, and said signal generating means being actuatable by the transmitted emitted fluorescent light.

10. The monitor of claim 9 that is arranged to sense resin leakage, wherein said probe means is disposed in a flow channel downstream of a filter, and where the signal generated by said monitor is used to induce recirculation of the effluent flow container said particles back through said filter when the signal is greater than a predetermined level.

11. A monitor for detecting the presence of ion exchange resin particles in a water flow channel that receives effluent from an ion exchange system, and for detecting the presence of single resin particles, comprising
   (a) probe means having a first window slit and disposed to inject a generally planar ribbon of rays of fluorescence-stimulating light through said first window slit and into a small volume of effluent in said channel,
   (b) detector means having a second window slit for restricting the amount of emitted fluorescent light that is transmitted and disposed to receive emitted fluorescent light from any particle in effluent passing through said small volume in said flow channel, said detector means being formed to detect rays of emitted fluorescent light that travel in a plane that is at an angle to the planar ribbon of rays of the injected light, and
   (c) signal generating means actuatable by the detected, emitted fluorescent light for generating a signal peak that is proportional to the size of a detected particle to indicate the presence of a particle in said effluent.

12. The monitor of claim 11 wherein the angle between said ribbon of injected light rays and the plane of rays of emitted fluorescent light that are detected is substantially a right angle.

13. The monitor of claim 11 wherein said window slits are disposed generally in parallelism with each other and along the direction of travel of said effluent.

14. The monitor of claim 13 wherein said small volume is defined by the intersections of imaginary planes that pass through said slits respectively.

15. The monitor of claim 11 wherein said probe means comprises a first bundle of optical fibers for transmitting light from a source to the injection site, and said detector means comprises a second bundle of optical fibers for tansmitting detected emitted light to said signal generating means.

* * * * *